United States Patent
Leach

(10) Patent No.: US 10,648,967 B2
(45) Date of Patent: May 12, 2020

(54) BREATH ALCOHOL IGNITION INTERLOCK DEVICE AND SYSTEM

(71) Applicant: Steven H. Leach, Toronto (CA)

(72) Inventor: Steven H. Leach, Toronto (CA)

(73) Assignee: Alcohol Countermeasure Systems (International) Inc., Toronto, Ontario (CA)

( * ) Notice: Subject to any disclaimer, the term of this patent is extended or adjusted under 35 U.S.C. 154(b) by 144 days.

(21) Appl. No.: 14/730,781

(22) Filed: Jun. 4, 2015

(65) Prior Publication Data
US 2015/0355162 A1    Dec. 10, 2015

Related U.S. Application Data

(60) Provisional application No. 62/008,095, filed on Jun. 5, 2014.

(51) Int. Cl.
*G01N 33/497*    (2006.01)

(52) U.S. Cl.
CPC ................. *G01N 33/4972* (2013.01)

(58) Field of Classification Search
CPC .................................. G01N 33/4972
USPC ............. 73/23.3; 180/272; 340/426.11, 576; 422/84; 600/532; 702/22–24
See application file for complete search history.

(56) References Cited

U.S. PATENT DOCUMENTS

| | | | | |
|---|---|---|---|---|
| 8,878,669 B2 * | 11/2014 | Nothacker | ............. | G08B 21/02 340/539.12 |
| 2009/0325639 A1 * | 12/2009 | Koehn | ................. | B60K 28/063 455/556.1 |
| 2011/0178420 A1 * | 7/2011 | Ridder | ............... | A61B 5/14546 600/532 |
| 2013/0282321 A1 * | 10/2013 | Son | ..................... | G01N 33/4972 702/104 |

OTHER PUBLICATIONS

Department of Transportation, National Highway Traffic Safety Administration, "Model Specifications for Breath Alcohol Ignition Interlock Devices (BAIIDs)", Federal Register, vol. 78, No. 89, published May 8, 2013, p. 26849-26867. (Year: 2013).*
Lifeloc Technologies, "An Evaluation of the Accuracy and Reliability of Popular Consumer Breathalyzers as Compared to Their Marketing Statements", p. 1-15. (Year: 2010).*

* cited by examiner

*Primary Examiner* — Daniel S Larkin
*Assistant Examiner* — Anthony W Megna Fuentes
(74) *Attorney, Agent, or Firm* — Head, Johnson, Kachigian & Wilkinson, PC

(57) ABSTRACT

The system for use with a breath tester includes a computing facility. In a learning mode, the facility is adapted to: receive the weight of a user; receive the details of each drink consumed by a user and the time of consumption of said each drink; receive measurements of breath alcohol content produced by the breath tester; and calculate the elimination rate of the user. In a predictive mode, the facility is adapted to: receive the details of each drink consumed by a user, and the time of consumption of said each drink; and calculate the expected breath alcohol content of the user based on the weight of the user, the calculated elimination rate of the user and said details of each drink consumed by the user and said time of consumption of said each drink.

1 Claim, 1 Drawing Sheet

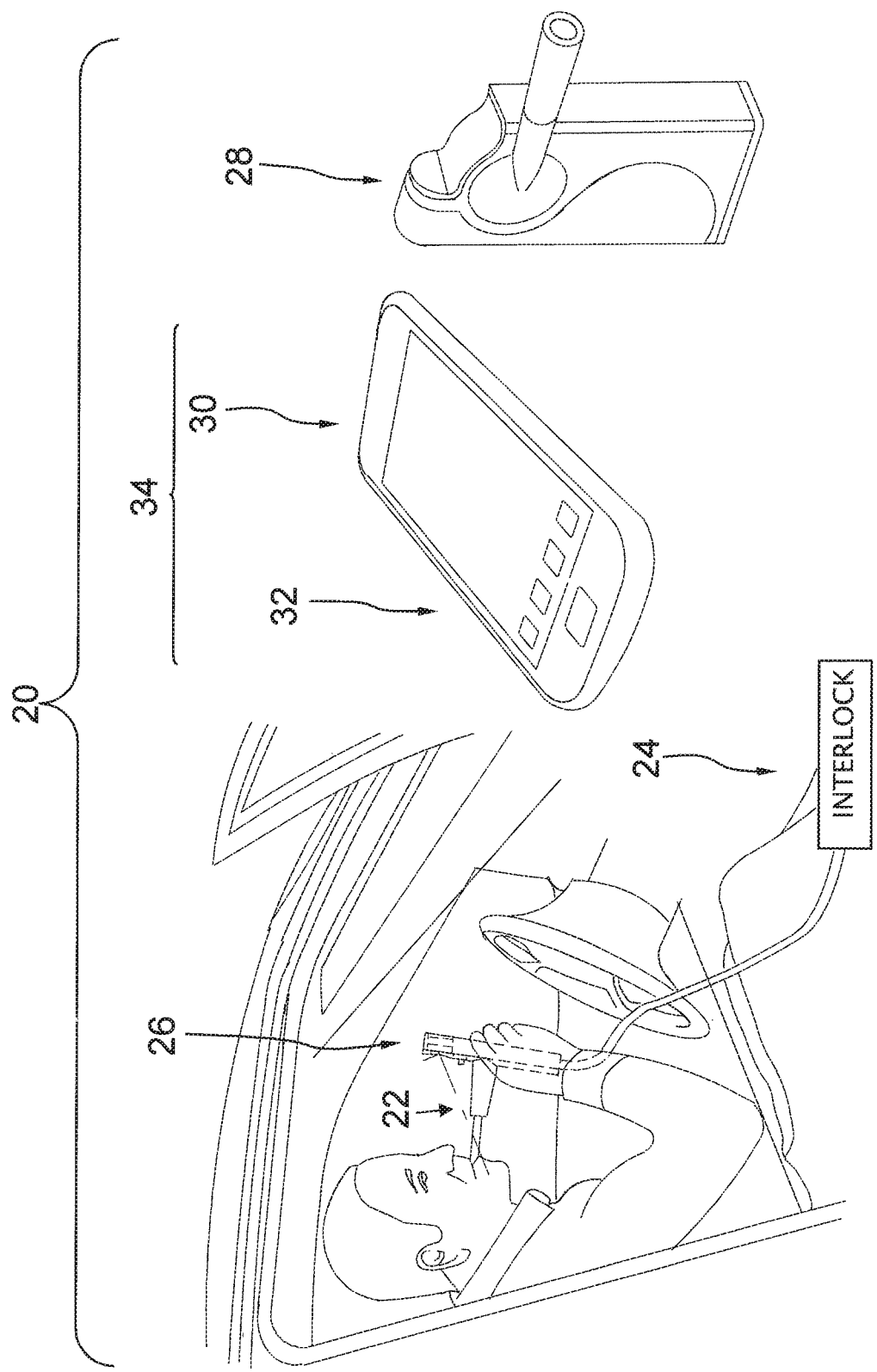

BREATH ALCOHOL IGNITION INTERLOCK DEVICE AND SYSTEM

CROSS-REFERENCE TO RELATED APPLICATION

This application claims priority to U.S. Provisional Patent Application Ser. No. 62/008,095, filed Jun. 5, 2014, which is herein incorporated by reference.

BACKGROUND OF THE INVENTION

1. Field of the Invention

The present invention relates to the field of breath alcohol testers.

2. Prior Art

In many jurisdictions, it is illegal to operate a vehicle while under the influence of alcohol.

In some jurisdictions, a person who has been convicted of driving under the influence of alcohol is required, prior to recovery of full driving privileges, to participate in a program which involves the temporary installation of a breath alcohol ignition interlock device [BAIID] in his or her vehicle. The BAIID is capable of receiving and analyzing a breath sample, to determine the extent to which the person giving the sample is under the influence of alcohol, and renders the vehicle disabled until a satisfactory breath sample is delivered; in this context, "satisfactory" typically means a sample that shows alcohol below a predetermined limit and that appears to have been delivered by a human [temperature, humidity, etc.]

It is commonplace for the breath alcohol tester portion of the BAIID to be tethered to the interlock portion of the BAIID by a physical link. However, in recent years, breath alcohol testers have become smaller, thereby to permit this part of the device to be a separate, hand-held, battery-powered device, that communicates with the interlock portion of the device by wireless connection. This can have some advantages in terms of economies of scale; certain manufacturers make two variants of the same hand held device, one which is used as a hand held personal breath alcohol tester, the other being used as part of a BAIID.

It is relatively rare for a manufacturer to make allowances that would permit the breath alcohol tester portion of a BAIID device to be used for personal breath test purposes; normally, this is discouraged, since breath samples that evidence breath alcohol in excess of the threshold amount permitted by a jurisdiction are viewed as failed attempts, and can prolong the period in which an offender is required to remain on the program.

Users who wish to avoid "fails" can purchase personal breath testers; however, good quality breath testers are relatively expensive, and persons that are already bearing the cost of a good quality breath tester [in the BAUD] are relatively less able to bear this cost, and often do without.

SUMMARY OF THE INVENTION

Forming one aspect of the invention is a system for use with a breath alcohol tester.

The system comprises a computing facility.

The computing facility has a learning mode and a predictive mode.

The facility is adapted, in the learning mode,
to receive the weight of a user;
to receive: the details of each drink consumed by a user, and the time of consumption of said each drink; and
measurements of breath alcohol concentration produced by the breath tester; and
to calculate the elimination rate of the user.

The facility is adapted, in the predictive mode,
to receive the details of each drink consumed by a user, and the time of consumption of said each drink; and
to calculate the expected breath alcohol concentration of the user based on the weight of the user, the calculated elimination rate of the user and said details of each drink consumed by the user and said time of consumption of said each drink.

According to other aspects of the invention, in the learning mode, the computing facility can be adapted to receive details of food consumed by the user and calculate the absorption rate of the user; and in the predictive mode, the computing facility can be adapted to calculate the expected breath alcohol concentration of the user using the calculated absorption rate.

According to another aspect of the invention, the computing facility can be adapted to receive details of drinks consumed in real time via a menu-driven software program.

According to another aspect of the invention, the computing facility can be adapted to receive details of food consumed in real time via a menu-driven software program.

According to another aspect of the invention, the computing facility can be defined by an app and a smart phone.

According to another aspect of the invention, the breath alcohol tester can be coupled by wireless connection to the smart phone in use and breath alcohol measurements made by the tester can be collected automatically by the smart phone for use in the calculations.

According to another aspect of the invention, in the predictive mode, the calculation of breath alcohol concentration can be based at least in part on recent breath alcohol measurements collected by the tester.

According to another aspect of the invention, the calculation can be based at least in part on the weight of the user, the calculated elimination rate of the user, details of each drink consumed by the user and said time of consumption of said each drink, previous breath alcohol concentration measurements collected by the tester and the accuracy of the tester.

According to another aspect of the invention, the computing functionality can warn the user when the calculation suggests that a threshold breath alcohol concentration associated with impairment may have been reached.

According to another aspect of the invention, the computing functionality can be adapted to receive a desired travel time window from the user and warn the user when the calculation suggests that further consumption of alcohol may cause the breath alcohol content of the user to remain in excess of the threshold when the travel time window is reached.

According to another aspect of the invention, the computing functionality can be adapted to receive a desired travel time window from the user and provide a prediction as to the maximum quantity of alcohol that can be consumed by the user at a steady rate of consumption in the period preceding the desired travel time window without causing the breath alcohol to exceed the threshold at any point in the travel time window.

According to another aspect of the invention, the computing functionality can be adapted to provide the user a predicted time at which point the breath alcohol content of the user is expected to fall below the threshold, assuming no further alcohol is consumed.

An improved breath alcohol ignition interlock device forms another aspect of the invention.

The device is of the type including a breath alcohol test facility, an arrangement that renders a vehicle in which the device is deployed disabled until a satisfactory breath sample is delivered to the breath alcohol test facility and a logger that maintains a record of both satisfactory and unsatisfactory breath samples delivered to the breath alcohol test facility. The improvement comprises a computing facility adapted to in a learning mode:
  receive the weight of a user;
  receive: the details of each drink consumed by a user, and the time of consumption of said each drink; and measurements of breath alcohol content produced by the breath alcohol facility; and
  calculate the elimination rate of the user; and
in a predictive mode,
  receive the details of each drink consumed by a user, and the time of consumption of said each drink; and
  calculate the expected breath alcohol content of the user based on the weight of the user, the calculated elimination rate of the user and said details of each drink consumed by the user and said time of consumption of said each drink.

According to another aspect of the invention, the breath alcohol facility can be a wireless, hand-held, battery-powered portable unit that communicates with the arrangement portion of the device by a wireless connection that is created automatically when the unit is in wireless range of the arrangement.

According to another aspect of the invention, the delivery of an unsatisfactory breath sample to the unit while the unit is coupled to the arrangement by wireless connection can be logged.

According to another aspect of the invention, the delivery of an unsatisfactory breath sample to the unit in circumstances wherein a wireless connection between the unit and device is not in existence can not be logged.

According to another aspect of the invention, the breath alcohol test facility can include:
  a breath alcohol tester associated with the arrangement portion of the device; and a remote breath alcohol tester; and the computing facility can collect and use data from both the breath tester associated with the arrangement portion and the remote breath alcohol tester.

According to another aspect of the invention, the remote breath alcohol tester can be a wireless, hand-held, battery-powered portable unit that communicates with the arrangement portion of the device by wireless connection that is created automatically when the unit is in wireless range of the arrangement.

According to another aspect of the invention, the delivery of an unsatisfactory breath sample to the unit while the unit is coupled to the arrangement by wireless connection can be logged.

According to another aspect of the invention, the delivery of an unsatisfactory breath sample to the unit in circumstances wherein a wireless connection between the unit and device is not in existence can not be logged.

According to another aspect of the invention, the calculation can take into account the weight of the user, the calculated elimination rate of the user, details of each drink consumed by the user and said time of consumption of said each drink, previous breath alcohol content measurements collected and the accuracy of the breath alcohol tester from which the measurement was collected.

According to another aspect of the invention, the computing functionality can warn the user when the calculation suggests that a threshold breath alcohol concentration associated with an unsatisfactory breath sample may have been reached.

According to another aspect of the invention, the computing functionality can be adapted to receive a desired travel time window from the user and warn the user when the calculation suggests that further consumption of alcohol may cause the breath alcohol content of the user to remain in excess of the threshold when the travel time window is reached.

BRIEF DESCRIPTION OF THE DRAWINGS

FIG. 1 is a simplified graphic depiction of a breath alcohol tester, a computing facility, and a remote breath alcohol testing unit in accordance with the present invention.

DETAILED DESCRIPTION OF THE PREFERRED EMBODIMENTS

The embodiments discussed herein are merely illustrative of specific manners in which to make and use the invention and are not to be interpreted as limiting the scope of the instant invention.

While the invention has been described with a certain degree of particularity, it is to be noted that many modifications may be made in the details of the invention's construction and the arrangement of its components without departing from the spirit and scope of this disclosure. It is understood that the invention is not limited to the embodiments set forth herein for purposes of exemplification.

An improved breath alcohol ignition interlock device 20 forms an exemplary embodiment of the invention.

The interlock device will be seen to be of the general type including a breath alcohol tester 22, an arrangement 24 that renders a vehicle in which the device is deployed disabled until a satisfactory breath sample is delivered to the breath alcohol tester and a logger 26 that maintains a record of both satisfactory and unsatisfactory breath samples delivered to the breath alcohol tester.

The improvement comprises:
  a remote breath alcohol testing unit 28 [in addition to the breath alcohol tester associated with the arrangement portion of the device]
  a system including
    a computing facility 30
    modifications to the logger; and
    a warning facility 32

The exemplary remote breath alcohol tester 28 is a wireless, hand-held, battery-powered portable unit that communicates with the arrangement portion of the device by wireless connection that is created automatically when the unit is in wireless range of the arrangement.

The exemplary computing facility is defined by a smart phone 34 having loaded thereon an app phone and has a learning mode and a predictive mode.

In the learning mode, the computing facility is adapted to:
  receive the sex, weight and age of a user;
  receive: in real time, via a menu-driven software program, the details of each drink consumed by a user, and the time of consumption of said each drink; the details of foods consumed and the times of consumption; and measurements of breath alcohol content produced by the remote breath alcohol tester and the breath alcohol tester associated with the arrangement portion of the device;

calculate the elimination rate of the user; and calculate the absorption rate of the user.

In the predictive mode, the facility is adapted to:

receive: in real time, via a menu-driven software program, the details of each drink consumed by a user, and the time of consumption of said each drink and the details of foods consumed and the times of consumption; and measurements of breath alcohol content produced by the remote breath alcohol tester and the breath alcohol tester associated with the arrangement portion of the device;

calculate the expected breath alcohol content of the user based on the sex, weight and age of the user, the calculated elimination and absorption rates of the user, the details of the food and drink consumed by the user and said time of consumption;

measurements of breath alcohol content produced by the remote breath alcohol tester and the breath alcohol tester associated with the arrangement portion of the device; and the accuracy of the breath tester(s) from which the measurement(s) were collected.

In terms of the specifics of the above, persons of ordinary skill will readily understand that the creation of an app that collects, in real time, details of food and drink consumed, is a matter of routine. By way of example, only, a suitable app is that made available at www.myfitnesspal.com.

Persons of ordinary skill will also readily understand that the delivery of breath alcohol data via wireless connection from a remote, battery-powered breath alcohol tester is a matter of routine.

Finally, persons of ordinary skill readily appreciate that the calculation of breath alcohol, taking into account weight, sex, age, and food and alcohol consumed, is easily done using conventional statistic analysis techniques and based upon Ueno's formula, Widmark's formula or combinations thereof.

In the exemplary embodiment, the logger is modified such that: the delivery of an unsatisfactory breath sample to the unit while the unit is coupled to the arrangement by wireless connection is logged; and the delivery of an unsatisfactory breath sample to the unit in circumstances wherein a wireless connection between the unit and device is not in existence is not logged.

The exemplary warning facility is a subroutine associated with the computing functionality which causes the computing functionality to warn the user when the calculation suggests that a threshold breath alcohol concentration associated with an unsatisfactory breath sample may have been reached [or will likely be reached, given expected absorption rates]. In another aspect of the warning facility, the computing functionality is adapted to receive a desired travel time window from the user and the computing facility warns the user when the calculation suggests that further consumption of alcohol may cause the breath alcohol content of the user to remain in excess of the threshold when the travel time window is reached.

In this specification and in the accompanying claims, it will be understood, for greater clarity, that a "desired travel time window" means a window of time in which travel is desired to occur, i.e. if the user wishes to drive his or her vehicle home after a restaurant dinner that is expected to conclude at 8 pm, give or take a half hour, and the drive is expected to take 30 minutes plus or minus 15 minutes, the "desired travel time window" would be 7:30 pm to 9:15 pm.

It will be evident that the above provides significant advantage, in that it maintains all of the existing advantages associated with conventional breath alcohol ignition interlock devices;

gives users the ability to better understand their alcohol tolerance without significantly increasing the risk of an adverse breath test appearing in their logs; and is relatively low cost, in that it can be used with relatively low-cost [and low-precision] solid state breath testers [for the remote device].

By way of further explanation, it will be appreciated that by coupling the convenience of an inexpensive, portable, but low-precision breath alcohol tester with the precision of an offender-quality breath alcohol tester, as well as the calibration provided by the computing facility, users obtain benefits similar to those obtained from the possession of a BAIID and a high-precision personal breath tester, at costs only slightly in excess of those associated with the BAIID itself.

Whereas but a single embodiment is herein described, variations are possible.

For example, whereas the previous description contemplates an improved device as a vendible, it will be evident that the invention could be configured as a system for use with a breath alcohol tester, i.e. including a computing facility defined, for example, by an app and a smart phone.

For example, whereas the exemplary embodiment takes account of food consumption, age, sex and weight of the user, this is not essential. The typical elimination rate of any given user could, instead, be learned by the device, through alcohol consumption followed by testing.

As well, whereas in the exemplary embodiment the breath alcohol measurements are relayed automatically to the computing facility, this is not essential; these could, for example, be entered manually.

As well, whereas the exemplary embodiment contemplates a second, low-cost, low-precision remote, the invention could be embodied with a high-precision, remote handheld, which would serve the same functions as the remote as well as the breath alcohol tester that is associated with the BAIID. In this case, all breath samples given while the unit was in the vicinity of the vehicle, i.e. in wireless range, would be logged.

Similarly, whereas the exemplary embodiment of the invention is configured as a BAUD, it will be evident that the invention could be embodied simply as the combination of a breath alcohol tester and a computing facility. This would provide many of the predictive benefits associated with the exemplary embodiment.

As yet another possibility, the offender-quality breath alcohol tester could be a vending machine, rather than the breath alcohol tester of the BAIID. This way, users obtain benefits similar to those obtained from the possession of a high-precision personal breath tester at costs similar to those associated with an inexpensive, portable, but low-precision breath alcohol tester.

Accordingly, the invention should be understood as limited only by the accompanying claims, purposively construed.

Whereas, the present invention has been described in relation to the drawings attached hereto, it should be understood that other and further modifications, apart from those shown or suggested herein, may be made within the spirit and scope of this invention.

What is claimed is:

1. An apparatus comprising: a computer system configured to in a learning mode, receive weight of a user; receive details of each drink consumed by the user, and time of consumption of said each drink;

and measurements of breath alcohol content; and calculate an elimination rate of the user; in a predictive mode, receive the details of each drink consumed by a user, and time of consumption of said each drink; and calculate expected breath alcohol content of the user based on the weight of the user, the calculated elimination rate of the user, said details of each drink consumed by the user and said time of consumption of said each drink; and receive a desired travel window from the user and warn the user when the calculated expected breath alcohol content suggests that further consumption of alcohol may cause the breath alcohol content of the user to remain in excess of a threshold when the travel window is reached.

\* \* \* \* \*